United States Patent

Sheehan et al.

[11] Patent Number: 5,312,990
[45] Date of Patent: May 17, 1994

[54] DI-AMINO COMPOUNDS

[75] Inventors: Michael T. Sheehan; James R. Sounik; Bret F. Hann, all of Corpus Christi; William W. Wilkison, III, Richardson, all of Tex.

[73] Assignee: Hoechst Celanese Corporation, Somerville, N.J.

[21] Appl. No.: 69,948

[22] Filed: May 28, 1993

[51] Int. Cl.$^5$ .......................................... C07C 217/44
[52] U.S. Cl. .................................. 564/348; 564/347; 564/353; 564/354
[58] Field of Search ............... 564/347, 348, 353, 354

[56] References Cited

U.S. PATENT DOCUMENTS

| | | | |
|---|---|---|---|
| 2,298,284 | 10/1942 | Emerson | 260/577 |
| 2,879,293 | 3/1959 | Goldberg et al. | 260/559 |
| 3,225,098 | 12/1965 | Krohs et al. | 260/570.8 |
| 3,366,684 | 1/1968 | Budd | 260/576 |
| 3,520,931 | 7/1970 | d'Ostrowick | 260/570.8 |
| 3,739,026 | 6/1973 | Wilson et al. | 260/576 |
| 3,928,603 | 12/1975 | Moreau et al. | 424/330 |
| 4,064,125 | 12/1977 | Krapcho | 564/354 X |
| 4,291,060 | 9/1981 | Kraska | 564/354 X |
| 4,293,557 | 10/1981 | Shibata et al. | 564/348 X |
| 4,388,250 | 6/1983 | Farber et al. | 260/465 F |
| 4,394,496 | 7/1983 | Schrader | 528/98 |
| 4,524,217 | 6/1985 | Davenport et al. | 564/223 |
| 4,663,485 | 5/1987 | Murphy et al. | 568/319 |
| 4,933,496 | 6/1990 | Fruchey | 568/337 |
| 4,994,613 | 2/1991 | Fruchey | 564/259 |
| 5,011,996 | 4/1991 | Kiel et al. | 564/321 |
| 5,021,429 | 6/1991 | Martin-Smith | 564/353 X |
| 5,047,592 | 9/1991 | Carpenter | 564/374 |
| 5,169,848 | 12/1992 | Bettarini et al. | 514/247 |

Primary Examiner—Richard L. Raymond
Attorney, Agent, or Firm—James J. Mullen; Donald R. Cassady

[57] ABSTRACT

Di-amines endowed with chain extension activity for formulations such as polyureas and polyurethanes are disclosed, and which have the general formula:

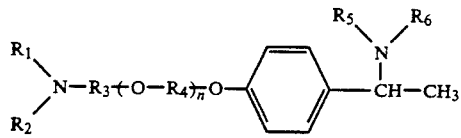

wherein n is 0–1000; $R_1$, $R_2$, $R_5$, and $R_6$ are each independently selected from the group consisting of H, —$CH_3$, —$CH_2CH_3$, —$CH_2OH$, and —$CH_2$—$CH_2$—OH; $R_3$=$R_4$, and $R_3$ and $R_4$ are from the group —$CH_2$—$CH_2$—; —$CH_2$—$C(CH_3)H$—; and —$C(CH_3)H$—$CH_2$—; and the diasteromeric salts thereof.

4 Claims, No Drawings

DI-AMINO COMPOUNDS

BACKGROUND OF THE INVENTION

1. Field of the Invention

The present invention relates to novel derivatives of 4-hydroxyacetophenone (4-HAP) to processes for preparing them, to polymer compositions which contain the novel compounds, and to the use of said compositions for a wide variety of end use applications.

2. Description of Related Art

The following prior art references are disclosed in accordance with the terms of 37 CFR 1.56, 1.97, and 1.98.

U.S. Pat. No. 5,169,848, issued Dec. 8, 1992, to Bettarini et al., discloses new pyridazinones endowed with insecticidal and acaricidal activity.

U.S. Pat. No. 3,520,931, issued Jul. 21, 1970, to d'Ostrowick et al., discloses a process for resolving a mixture of optical antipodes of a primary alphaarylalkylamine in which one of these antipodes predominates.

U.S. Pat. No. 5,011,996, issued Apr. 30, 1991, to Kiel et al., discloses reaction products of oxo compounds and amines or ammonia, such as α-(p-Chlorophenyl)ethylamine (Example 1 therein).

U.S. Pat. No. 4,394,496, issued Jul. 19, 1983, to Paul G. Schrader discloses polyglycidyl ethers of this (hydroxyphenyl) alkanes, their blends with other epoxy compounds, and their cured products.

U.S. Pat. No. 4,388,250, issued Jun. 14, 1983, to Farber et al., discloses a process for the preparation of p-Hydroxybenzyl-nitrites (note Table I, columns 7 and 8).

Other U.S. patents which have related application and may be of interest include U.S. Pat. Nos. 2,298,284; 3,366,684; 3,739,026; 3,225,098; 3,928,603; 5,047,592, and U.S. Pat. No. 4,394,496.

All of the above-cited prior art patents are incorporated herein by reference in their entirety.

ADDITIONAL BACKGROUND INFORMATION

Compounds belonging to the class of hydroxyacetophenones, processes for preparing the same, and their end use applications are disclosed in U.S. Pat. Nos. 4,663,485; 4,524,217; 4,933,496; and U.S. Pat. No. 4,994,613, the entire disclosures of which patents are incorporated herein by reference.

SUMMARY OF THE INVENTION

The present invention provides novel di-amino compounds ("NDC") endowed with chain extension activity for formulations such as polyurethanes and which have the general formula:

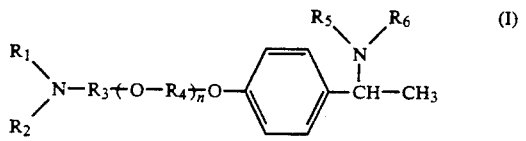

wherein n is 0-1000; and $R_1$, $R_2$, $R_5$, and $R_6$ are each independently selected from the group consisting of H, —$CH_3$, —$CH_2CH_3$, —$CH_2OH$, and —$CH_2$—$CH_2$—OH; $R_3$=$R_4$, and $R_3$ and $R_4$ are from the group —$CH_2$—$CH_2$—; —$CH_2$—$C(CH_3)H$—; and —$C(CH_3)H$—$CH_2$—; and the diasteromeric salts thereof.

DETAILED DESCRIPTION OF THE PREFERRED EMBODIMENTS

The present invention provides novel di-amino compounds (NDC) which are derivatives of 4-hydroxyacetophenone, a well-known basic building block for numerous organic compounds. These novel amines have the general formula as follows:

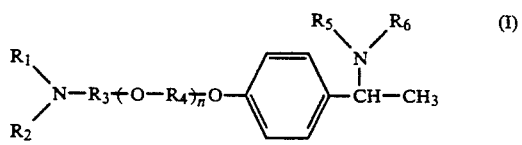

wherein:

n is 0 to 100 (preferably 0–100);

$R_1$, $R_2$, $R_5$, and $R_6$ are each independently selected from the group:

H

—$CH_3$

—$CH_2CH_3$

—$CH_2OH$

—$CH_2$—$CH_2$—OH; and $R_3$ equals $R_4$;

$R_3$ and $R_4$ represent a member from the group:

—$CH_2$—$CH_2$—

—$CH_2$—$C(CH_3)H$—

—$C(CH_3)H$—$CH_2$—

The compounds having the general formula (I) can be prepared by reacting an alkali metal salt of 4-hydroxyacetophenone (4-HAP) with an oxide material such as ethylene oxide or propylene oxide in the presence of a suitable catalyst and then subjecting the reaction product or oxylated material to full reductive amination under very high pressure and temperatures to form NDC having the above formula (I). This overall reaction scheme using ethylene oxide is shown as follows:

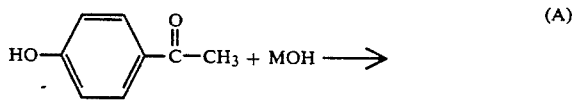

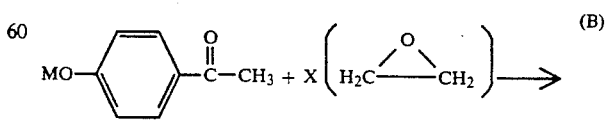

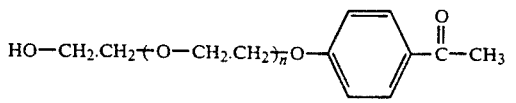

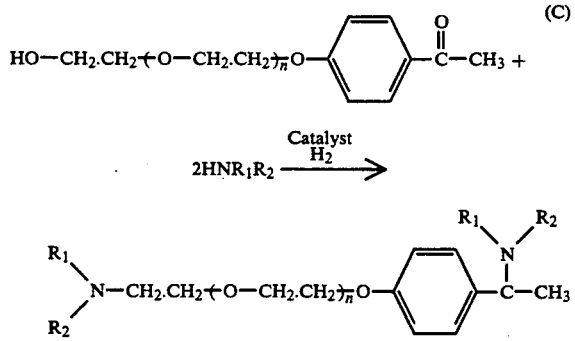

In equation (A), M is an alkali metal such as potassium.

In equation (B), X represents the number of molar equivalents of the ethylene oxide (or propylene oxide) used to form the chain, and n+1 equals X. n can be 0 to 1000, but are preferably from 0 to 100.

In equation (C), $HNR_1R_2$ is ammonia or a primary, or secondary amine having the same groups ($R_1$, $R_2$, $R_5$, and $R_6$), as hereinbefore described in formula (I).

In the formulation of the alkali metal salt of 4-HAP, equation (A), the reactants are mixed together in a reaction vessel along with a suitable inert solvent such as isopropanol and then heated at about 30° C. to about 100° C. for a sufficient period of time until all the solids are dissolved into the liquid. The resultant reaction mass is then allowed to cool to room temperature and then the desired alkali metal salt is allowed to crystalize over a period of time suitable to promote crystallization from the solution. The solid material, i.e. the 4-HAP salt is then separated from the mother liquor by any conventional means, such as filtration. The solid material is then washed with a suitable inert solvent such as heptane and then dried at a temperature of from about 30° C. to about 100° C., under vacuum, where so desired.

In conjunction with equation (B) above, the alkali metal salt of 4-HAP is charged into a reaction vessel along with preselected quantities of either ethylene oxide or propylene oxide and a suitable inert solvent such as dimethylformamide (DMF). The reaction vessel is provided with a condenser and a mechanical stirrer. The reaction mass is then slowly heated from room temperature (i.e. 20° C.) to about 100° C. over a period of time to insure that the ethoxylation of propoxylation takes place in the desired fashion. While this part of the process is conducted at atmospheric pressure, it is within the scope of the present invention to conduct this reaction under pressure, e.g. from about 20 psig to about 300 psig, and thus reduce the reaction times. After the reaction has taken place, the reaction mass is allowed to cool to room temperature and then a suitable de-salting agent, such as acetic acid, is added to this mass in order to remove and inactivate the alkali metal ion. This ion precipitates and the resultant suspension is separated from the mother liquor by any conventional means such as filtration. This liquid is then reduced under vacuum to an oil, and the oil is then distilled under vacuum and the fraction boiling between 130° C. and 210° C. is collected and represents the desired end product, i.e. the ethoxylated or propoxylated 4-HAP.

Referring to equation (C) above, the final NDC is obtained by the full reductive amination of the ethoxylated or propoxylated 4-HAP material ("E/P 4-HAP").

Specifically, NDC is prepared from E/P 4-HAP by contacting the E/P 4-HAP with ammonia or a primary or secondary amine ("amine") in the presence of a solvent, a co-catalyst, and an acid-promoted catalyst under conditions of temperature and pressure which allow the full reductive amination of E/P 4-HAP to form NDC to occur. In this manner, NDC is produced in very high yields.

In the process of the instant invention, it is preferred that excess ammonia or amine be used over that required to react with E/P 4-HAP. Thus, it is preferred that E/P 4-HAP and ammonia or amine be supplied in a molar ratio of from about 1:1 to about 1:10.

The term "acid-promoted" catalyst as used herein means a hydrogenation catalyst such as Raney nickel, Raney cobalt, palladium on carbon, and platinum on carbon.

It has also been discovered that the addition of a co-catalyst such as acetic acid and oxalic acid produces a marked improvement in the yield of NDC in the process using this "acid-promoted" catalyst. It is not understood exactly why the yield is substantially increased by the use of this co-catalyst with the other catalyst, and the result is unexpected and surprising.

The amount of "acid-promoted" catalyst used is at least five (5) percent by weight, based on the weight of the E/P 4-HAP supplied. Preferably, the catalyst present is from about ten (10) percent to about thirty (30) percent by weight, based on the weight of the E/P 4-HAP.

The acid-promoted catalyst can be in any form; e.g. lumps, filaments, tablets, pellets, granules, etc. It can also be used in crushed form or as a powder. The grains should be neither too fine nor too coarse. Coarse catalyst particles are undesirable because they have too small a surface area to adequately catalyze the reaction. On the other hand, fine-grained catalysts, although highly reactive due to their large surface area, are separated only with great difficulty by sedimentation, centrifugation, or filtration. The person of ordinary skill will know how to properly select the catalyst particle size.

The amount of co-catalyst used is at least one (1) percent by weight, based on the weight of the E/P 4-HAP supplied. Preferably, the co-catalyst present is from about one (1) percent to about ten (10) percent by weight, based on the weight of the E/P 4-HAP.

Before the reaction begins, the hydrogenation catalyst is suspended in a solvent. This solvent should be inert to the reaction taking place; i.e. it must not interfere with the hydrogenation. Suitable solvents are the reaction product itself; aliphatic, cycloaliphatic, aromatic hydrocarbons, ether, alcohols, and mixtures thereof. In many cases, cyclic ethers and/or aliphatic alcohols have particularly proven their worth. Solvents include polar liquids which can be used in accordance with the instant invention which include lower alkanols including cycloalkanols, e.g., those having from one (1) to eight (8) carbon atoms, such as methanol, ethanol, isopropanol, butanol, pentanol, cyclohexanol, and cyclobutanol, as well as polar asymmetrically halogenated hydrocarbons, e.g., those having from one (1) to eight (8) carbon atoms, such as chloroform, trifluorotrichloroethane, and trichlorofluoromethane, and mixtures of the above. Aliphatic alcohols having from one (1) to six (6) carbon atoms are desirable. Methanol, ethanol, propanol, i-propanol, n-butanol, and/or i- butanol have proven particularly successful. In view of their good solubility in water, methanol, ethanol, and/or propanols are strongly recommended. Methanol and/or ethanol and/or isopropanol have been found to be most suitable.

In preferred embodiments of the equation (C) above, the acid-promoted catalyst is charged into a suitable reaction vessel capable of being heated under pressure, such as an autoclave. The air in the reaction vessel is displaced, preferably by sweeping out the air with nitrogen, followed by hydrogen, after the reaction vessel is charged with a solvent. The reaction vessel is sealed, and the vessel and contents are then heated by any suitable means to a reaction temperature sufficient to promote reductive amination of the E/P 4-HAP in the presence of the acid-promoted catalyst and hydrogen. When the reaction temperature is reached, E/P 4-HAP, a co-catalyst, hydrogen and ammonia or amine are introduced into the autoclave to pressurize the reaction vessel and provide feed materials thereto. The reaction is continued, agitating the contents at the elevated reaction temperature and supplying additional hydrogen and ammonia or amine as needed to maintain the desired pressure within the reaction vessel until no further NDC is formed and the E/P 4-HAP is consumed. The reaction is usually complete in 3 to 20 hours.

The reaction is closely followed by removing samples periodically from the reaction vessel and analyzing the products by liquid chromatography. Further evidence that the reaction is complete is indicated by a static hydrogen pressure within the reaction vessel.

After the reaction has been determined to be complete, the reaction mixture is permitted to cool, the reaction vessel is opened, and the contents are discharged. At this point, the contents consist essentially of the acid-promoted catalyst and a solvent solution of NDC. The solvent solution of NDC is separated from the catalyst by any suitable means, such as by filtration or decantation. The NDC is recovered by reducing to an oil under vacuum.

In the past, alcoholic slurries of Raney metal catalysts having required special handling, as they are well known as being pyrophoric. If allowed to dry in air, a Raney metal catalyst will flare rapidly to red heat and provide an ignition source for exposed combustibles. This has presented a particular problem when charging batch reactors with such catalysts and when removing the product. Surprisingly, the acid-promoted Raney metal catalysts useful in this invention have been found to be non-pyrophoric. This property is unique and eliminates one of the chief hazards in the manufacture of amines by reductive amination.

In another embodiment of equation (C) above, the reaction solution is prepared by mixing said catalyst in a solvent such as isopropanol. Then the E/P 4-HAP and co-catalyst are fed into the reaction vessel. Generally, the concentration of E/P 4-HAP will vary from about thirty (30) to sixty (60) percent (weight basis) based upon the total weight of the reaction solution. Ammonia or amine is preferably added in an amount of from 3 to 10 moles of ammonia or amine for every mole of E/P4-HAP used. Ammonia or amine in excess of the stoichiometric amount is generally required. The solvent is present as an inert diluent and the amount of solvent can vary widely, but should not be used in an amount which would greatly increase recovery costs. It will be understood by those skilled in the art that the actual amounts of reactants used in this process will vary widely, depending upon the size of the equipment used in commercial production.

The reaction temperature for the reductive amination is preferably at least 150° C., preferably 175° C. to 350° C., and more preferably 200° C. to about 300° C. Within this range, excellent yields and reaction rates are obtained. Reaction temperatures much below 100° C. reduce the reaction rates and full reductive amination does not occur. The upper limit of reaction temperatures is dependent upon the equipment limitations.

When the reaction temperature is reached, hydrogen (in addition to ammonia or amine), is introduced into the autoclave to pressurize the reaction vessel to a total pressure preferably of at least 500 psi. Generally, the total pressure will be from 500 to 10,000 psi, preferably from about 2000 psi to about 3000 psi, as within this range, excellent yields and reaction rates are achieved. Pressures much below 500 psi reduce the reaction rates and full reductive amination does not occur. The upper pressure at which the process can be operated is limited only by the structural limitations of the equipment used.

It is also within the scope of the present invention to employ other reductive amination procedures disclosed in the art. One such procedure is described in U.S. Pat. No. 4,766,245 which is incorporated herein by reference in its entirety.

The di-amino compounds of this invention are particularly suited for reaction with isocyanates to manufacture articles by a Reaction Injection Molding (RIM) process. RIM is a technique for the rapid mixture and molding of large, fast-curing urethane parts. RIM polyurethane parts are used in a variety of exterior body applications on automobiles where the light weight contributes to energy conservation. RIM parts are generally made by rapidly mixing active hydrogencontaining materials with polyisocyanate and placing the mixture into a mold where reaction proceeds. After reaction and de-molding, the parts may be subjected to an additional curing step which comprises placing the parts in an oven, held at 250° F. or higher.

Surprisingly, it also has been found that the di-amino compounds of this invention are useful as curing agents in forming clear epoxy castings and adhesives with highly satisfactory physical properties. Such epoxy products find application in the electrical and electronic fields. These di-amino compounds also have been found to be suitable for use in polyamides, polyimides, and epoxy resins.

The following specific examples are supplied for the purpose of better illustrating the invention. These examples are not intended, however, to limit or restrict the scope of the invention in any way and should not be construed as providing conditions, parameters, or values which must be utilized exclusively in order to practice the present invention.

EXAMPLE 1

Synthesis of Potassium Salt of 4-Hydroxyacetophenone

A mixture of 4-hydroxyacetophenone (556 g), potassium hydroxide (273 g), and isopropanol (3 L) is charged to a 5 L glass reactor fitted with a condenser and mechanical stirrer. The mixture is heated until all of the solids are dissolved (80° C.). The solution is then cooled to room temperature and the product is allowed to crystallize for 12 hours. The solid is isolated by filtration, washed with heptane (1 L), and dried under vacuum (60 torr., 50° C.). The product is a light yellow solid and weighed 610 g (86%). This reaction is representative of equation (A) above.

EXAMPLE 2

A mixture of potassium 4-acetyl phenolate (313 g), propylene oxide (507), and DMF (900 ml) is charged to a 3 L glass reactor fitted with a condenser and mechanical stirrer. The reaction is heated and the temperature slowly increases from 52° C. to 82° C. over a period of 3 hours. The mixture is cooled to room temperature and acetic acid (108 g) is slowly added. The suspension is filtered and the filtrate is reduced under vacuum to an oil. The oil is distilled under vacuum (0.5 torr.) and the fraction boiling between 140° C. to 205° C. is collected. The product is a clear, colorless liquid and weighs 284 g (63%). Typical physical properties are given in Table I. This reaction is representative of equation (B) above, except that propylene oxide is used instead of ethylene oxide.

TABLE I

Typical Properties of Propoxylated 4-Hydroxyacetophenone

| Property | Propoxylated 4-Hydroxyacetophenone (wt %) |
| --- | --- |
| Average n | |
| n = 0 | 12.58 |
| n = 1 | 76.08 |
| n = 2 | 11.34 |
| n = 3 | — |
| Molecular Weight (Average) | 251.28 |
| Boiling Range | 140–193° C. (<1 torr.) |
| Density (@ 27° C.) | 1.094 g/mL |
| Color | Clear, Colorless Liquid |
| Solubility (>5 wt %) | |
| Water | No |
| Acetone | Yes |
| Methanol | Yes |
| N,N-Dimethylformamide | Yes |
| Heptane | No |
| Ethyl Acetate | Yes |

EXAMPLE 3

In a 100 cc stainless steel, high pressure reactor, a solution of propoxylated 4-hydroxyacetophenone (10 g, 0.04 moles), and glacial acetic acid (0.5 g, 8 mmoles) in isopropanol (30 g, 0.4 moles), and Raney Nickel catalyst (1.1 g) were charged. The reactor is purged 3 times with nitrogen (100 psi) and then evacuated to approximately 30 torr. Then anhydrous ammonia (7.3 g, 0.4 moles) is charged while maintaining the reactor temperature below 30° C. The reactor is heated and maintained at 240° C. for 1.5 hours. Hydrogen is then charged to a pressure of 2500 psi. The temperature is maintained at 240° C. for 2 hours at a constant hydrogen pressure of 2500 psi. The reactor is cooled to 40° C. and then discharged. The pressure of 2500 psi. The reactor is cooled to 40° C. and then discharged. The ammonia is removed under vacuum and the product reduced to an oil under vacuum and weighed (9.1 g, 0.36 moles, 91%). A similar product (14.9 g) was vacuum distilled (152° C. to 168° C., 0.5 torr.) and weighed (7.4 g, 42%). The product is a clear, colorless oil. This reaction is representative of equation (C) above, except that the 4-HAP derivative used is propoxylated instead of ethoxylated.

EXAMPLE 4

In a 100 cc stainless steel high pressure reactor, a solution of propoxylated 4-hydroxyacetophenone (10 g, 0.04 moles) in isopropanol (35 g, 0.58 moles), alumina (1.0 g), and palladium on carbon catalyst (50% $H_2O$)(2.0 g) were charged. The reactor is purged 3 times with nitrogen (100 psi) and then evacuated to approximately 30 torr. Then anhydrous ammonia (16.2 g, 1.0 moles) is charged while maintaining the reactor temperature below 30° C. The reactor is heated and maintained at 250° C. for 1.5 hours. Hydrogen is then charged to a pressure of 2500 psi. The temperature is maintained at 250° C. for 2 hours at a constant hydrogen pressure of 2500 psi. The reactor is cooled to 40° C. and then discharged. The ammonia is removed under vacuum and the product reduced to an oil under vacuum and weighed (9.3 g, 0.36 moles, 92%). This reaction is representative of equation (C) above, except that the 4-HAP derivative used is propoxylated instead of ethoxylated.

EXAMPLES 5–20

Using the procedures set forth in Examples 1–4 above, the compounds reported in Table II are obtained.

TABLE II

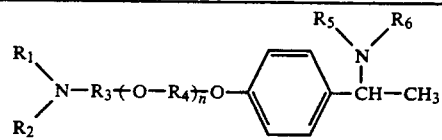

| Example | $R_3/R_4$ | n (Average) | $R_1/R_2$ | $R_5R_6$ |
| --- | --- | --- | --- | --- |
| 5 | $-CH_2-CH_2-$ | 2 | H | H |
| 6 | $-CH_2-CH_2-$ | 8 | H | H |
| 7 | $-CH_2-CH_2-$ | 72 | H | H |
| 8 | $-CH_2-CH_2-$ | 4 | $-CH_3$ | $-CH_3$ |
| 9 | $-CH_2-CH_2-$ | 3 | $-CH_2-CH_3$ | $-CH_2CH_3$ |
| 10 | $-CH_2-CH_2-$ | 3 | $-CH_2OH$ | $-CH_2OH$ |
| 11 | $-CH_2-CH_2-$ | 3 | $-CH_2CH_3$ | $-CH_2OH$ |
| 12 | $-CH_2-CH_3-$ | 4 | $-CH_2-CH_2-OH$ | $-CH_2-CH_2-OH$ |
| 13 | $-CH_2-C(CH_3)H-$ | 2 | H | H |
| 14 | $-CH_2-C(CH_3)H-$ | 2 | $-CH_3$ | $-CH_3$ |
| 15 | $-CH_2-C(CH_3)H-$ | 2 | $-CH_2CH_3$ | $-CH_2CH_3$ |
| 16 | $-CH_2OC(CH_3)H-$ | 2 | $-CH_2OH$ | $-CH_2OH$ |
| 17 | $-CH_2-C(CH_3)H-$ | 6 | $-CH_2CH_3$ | $-CH_2OH$ |
| 18 | $-CH_2-C(CH_3)H-$ | 4 | $-CH_2-CH_2-OH$ | $-CH_2-CH_2-OH$ |
| 19 | $-C(CH_3)H-CH_2-$ | 3 | H | $-CH_3$ |
| 20 | $-C(CH_3)H-CH_2-$ | 3 | H | $-CH_2OH$ |

EXAMPLE 21

Synthesis of a Polyurea with NDC

A 2.0 g sample (0.012 mole) of tolylenediisocyanate (an 80:20 mixture of 2,4 and 2,6 tolylenediisocyanate) is mixed carefully with a 3.0 g sample (0.011 mole) of the diamino product prepared according to the procedure in Example 4 above. The mixture thickens and hardens to a glassy resin with the generation of heat. The material is a hard, clear, amber solid and is found to be suitable for use in automobile parts.

EXAMPLES 22-28

Preparation of Polyurethanes Containing NDC

Polyurethanes are prepared incorporating NDC by substitution of NDC for other polyols present in a reaction mixture. Examples are described in the Encyclopedia of Polymer Science & Engineering, Volume 1, pgs. 243-303 (2nd Edition, 1988, Wiley). As used herein, the term, "polyurethane" refers to materials that include the carbamate function as well as other functional groups such as ester, ether, amide, and urea. Polyurethanes are usually produced by the reaction of a polyfunctional isocyanate with a polyol or other hydroxyl-containing reactant. Since the functionality of the hydroxyl-containing reactant or the isocyanate can be adjusted, a wide variety of branched or cross-linked polymers can be formed. The hydroxyl-containing component may be of a wide variety of branched or cross-linked polymers can be formed. The hydroxyl-containing component may be of a wide variety of molecular weights and types including polyester and polyester polyols. The polyfunctional isocyanates may be aromatic, aliphatic, cycloaliphatic, or polycyclic in structure and can be used directly as produced or modified. The flexibility in reactants leads to the wide range of physical properties of available materials. Present invention polymers are prepared by substituting NDC for a portion of the hydroxyl-containing reactant in a mole ratio of NDC/hydroxyl from about 0.001:1 to about 1:1 for the polyol in a polyurethane reaction mixture or, in other words, from about 0.05 to about 50 mole percent of the total mixture as described above in connection with Example 21. Specifically, Example 21 is repeated using the NDC compounds from Examples 10, 11, 12, 16, 17, 18, and 20. The resultant polyurethane compositions are found functional in a wide variety of automobile parts.

In conjunction with the novel di-amino compounds (NDC) falling within the general structural formula (I) above, each of these compounds contains a chiral carbon atom and, consequently, is a racemate which consists of two mirror-image forms (enantiomers). Where one so desires to provide and/or use only one or single enantiosmer thereof, it is within the scope of the present invention that this can be accomplished by means well-known in chirotechnology such as optical resolution by known resolving agents such as chiral acids. Examples of chiral acids include, without limitation thereof, tartaric acid, molic acid, camphorsulfonic acid, lactic acid, bromocamphorsulfonic acid, mandelic acid, 2-(4-isobutyl-phenyl)-propionic acid (ibuprofen), and derivatives thereof. The use of these chiral acids with the novel di-amino compounds (NDC) provides the diasteromeric salts thereof.

It has also been found that the tertiary amines falling within the general structural formula (I) above, exhibit the capacity to act as a catalysts for polyurethanes.

What is claimed is:

1. Di-amino compounds having the structural formula (I):

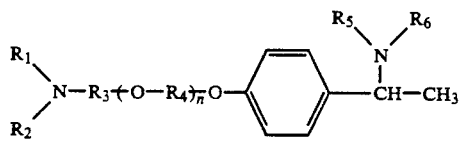

wherein n is 1-1000; $R_1$, $R_2$, $R_5$, and $R_6$ are each independently selected from the group consisting of H, —$CH_3$, —$CH_2CH_3$, —$CH_2OH$; and —$CH_2$—$CH_2$—OH; and $R_3=R_4$ and $R_3$ and $R_4$ are from the group —$CH_2$—$CH_2$—; —$CH_2$—$C(CH_3)H$—; and —$C(CH_3)H$—$CH_2$—; and the diasteromeric salts thereof.

2. Di-amino compounds having the structural formula (II):

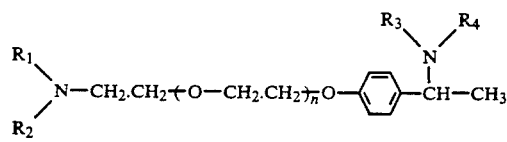

wherein n is 1-1000; and $R_1$, $R_2$, $R_3$, and $R_4$ are each independently selected from the group consisting of H, —$CH_3$, —$CH_2CH_3$, —$CH_2OH$; and —$CH_2$—$CH_2$—OH; and the diasteromeric salts thereof.

3. Di-amino compounds having the structural formula (III):

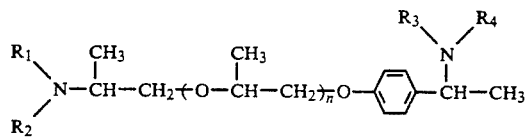

wherein n is 1-1000; and $R_1$, $R_2$, $R_3$, and $R_4$ are each independently selected from the group consisting of H, —$CH_3$, —$CH_2CH_3$, —$CH_2OH$; and —$CH_2$—$CH_2$—OH; and the diasteromeric salts thereof.

4. Di-amino compounds having the structural formula (IV):

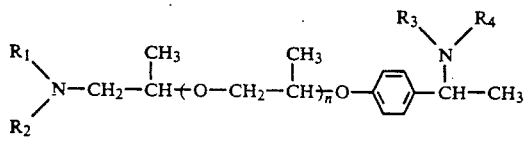

wherein n is 1-1000; and $R_1$, $R_2$, $R_3$, and $R_4$ are each independently selected from the group consisting of H, —$CH_3$, —$CH_2CH_3$, —$CH_2OH$; and —$CH_2$—$CH_2$—OH; and the diasteromeric salts thereof.

* * * * *